(12) United States Patent
Kong et al.

(10) Patent No.: US 9,993,509 B2
(45) Date of Patent: Jun. 12, 2018

(54) METHOD FOR REGULATING BLOOD GLUCOSE LEVEL

(71) Applicant: SINPHAR PHARMACEUTICAL CO., LTD., Yilan County (TW)

(72) Inventors: Zwe-Ling Kong, Yilan County (TW); Fan-Chi Ko, Yilan County (TW); Ai-Ling Yeh, Yilan County (TW)

(73) Assignee: SINPHAR PHARMACEUTICAL CO., LTD., Yilan County (TW)

( * ) Notice: Subject to any disclaimer, the term of this patent is extended or adjusted under 35 U.S.C. 154(b) by 149 days.

(21) Appl. No.: 14/946,343

(22) Filed: Nov. 19, 2015

(65) Prior Publication Data

US 2016/0082064 A1    Mar. 24, 2016

Related U.S. Application Data

(62) Division of application No. 14/289,035, filed on May 28, 2014, now Pat. No. 9,339,522.

(Continued)

(51) Int. Cl.
*A61K 31/7016*    (2006.01)
*A61K 31/7028*    (2006.01)
(Continued)

(52) U.S. Cl.
CPC ............ *A61K 36/64* (2013.01); *A61K 31/702* (2013.01); *A61K 31/7016* (2013.01); *A61K 31/7028* (2013.01); *C07H 15/18* (2013.01)

(58) Field of Classification Search
None
See application file for complete search history.

(56) References Cited

U.S. PATENT DOCUMENTS 7,087,252 B2 *   8/2006   Tu .......................... A61K 31/70
                                                                 424/725
2010/0242139 A1    9/2010   Sinclair et al.

FOREIGN PATENT DOCUMENTS

CN        1268341        8/2006
CN        100131391 2    12/2008
(Continued)

OTHER PUBLICATIONS

Adebajo et al., Planta Medica, 2007, vol. 73(3), pp. 241-250.*

(Continued)

*Primary Examiner* — Traviss C McIntosh, III
(74) *Attorney, Agent, or Firm* — Ping Wang; Morris, Manning & Marlin, LLP

(57) ABSTRACT

A method for increasing the expression of SIRT1 mRNA and/or decreasing the expression of SOCS3 mRNA, and especially for regulating blood glucose levels in a subject in need thereof is provided. The method comprises administering to the subject an effective amount of an active component selected from the group consisting of a compound of formula (I), a pharmaceutically acceptable salt of the compound of formula (I), and combinations thereof:

(I)

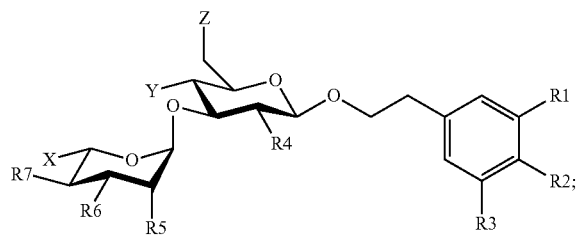

wherein X is H or C1-C3 alkyl; one of Y and Z is

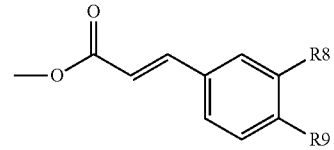

and the other one is H, OH or

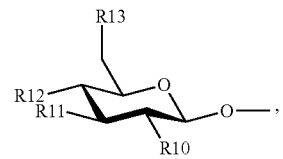

wherein when Y is

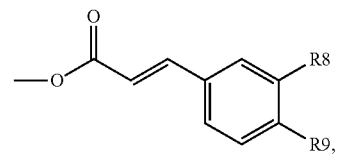

Z is

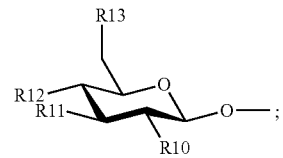

R1 to R13 are independently H or OH, and wherein, R1 to R3 are not simultaneously H; R8 and R9 are not simultaneously H.

8 Claims, 6 Drawing Sheets

Related U.S. Application Data (60) Provisional application No. 61/828,724, filed on May 30, 2013.

(51) Int. Cl.
*A61K 36/64* (2006.01)
*A61K 31/702* (2006.01)
*C07H 15/18* (2006.01)

(56) References Cited

FOREIGN PATENT DOCUMENTS

| | | |
|---|---|---|
| CN | 101 964 994 | 12/2010 |
| CN | 102283854 | 12/2011 |
| CN | 102 716 342 | 10/2012 |
| CN | 102716342 | 10/2012 |
| CN | 102861041 | 1/2013 |
| CN | 101301298 | 4/2013 |
| JP | H03 271227 | 12/1991 |
| JP | 2009-196905 | 9/2009 |
| JP | 2009263279 | 11/2009 |
| JP | 2014084319 | 5/2014 |
| WO | 2008093678 | 8/2008 |

OTHER PUBLICATIONS

Miyuki, I. et al., "Antidiabetic Effect of Desert Ginseng Clstanche Tubulosa (*Clstanche tubulosa*, fleshy stem)", Japan Society of Nutrition and Food Science, 2012, vol. 66, pp. 139 (2K-09p).

Adebajo, A. C. et al., "Hypoglycaemic constituents of *Stachytarpheta cayennensis* leaf", Planta Med., 2007, vol. 73 (3), pp. 241-250.

Morikawa, T. et al., "Acylated phenylethanoid oligoglycosides with hepatoprotective activity from the desert plant *Cistanche tubulosa*", Bioorganic & Medicinal Chemistry, 2010, vol. 18(5), pp. 1882-1890.

Moynihan, K. A. et al., "Increased dosage of mammalian Sir2 in pancreatic beta cells enhances glucose-stimulated insulin secretion in mice", Cell Metabolism, 2005, vol. 2(2), pp. 105-117.

Hawley, J. A. et al., Physical Activity and Type 2 Diabetes, 2008, p. 96.

Preethi, P.J., "Herbal Medicine for Diabetes Mellitus: A Review", International Journal of Phytopharmacy, 2013, vol. 3(1), pp. 1-22.

Boudjelal, A. et al., "Compositional analysis and in vivo anti-diabetic activity of wild Algerian *Marrubium vulgare* L. infusion", Fitoterapia, 2012, vol. 83(2), pp. 286-292.

File History of U.S. Appl. No. 14/289,035, filed May 28, 2014.

Maisky, V.V. et al., Elementary pharmacology, 2009, pp. 332-333 and 336.

* cited by examiner

METHOD FOR REGULATING BLOOD GLUCOSE LEVEL

This application is a Divisional of U.S. application Ser. No. 14/289,035, filed on May 28, 2014, which claims benefit to U.S. Application Ser. No. 61/828,724, filed on May 30, 2013. The entirety of the aforementioned applications is incorporated herein by reference.

BACKGROUND OF THE INVENTION

Field of the Invention

The present invention relates to a method for increasing the expression of SIRT1 mRNA and/or decreasing the expression of SOCS3 mRNA, and especially for regulating the blood glucose level in a subject in need thereof and to a medicament for such treatment, and especially relates to the use of an active component available from an *Cistanche tubulosa* extract in the treatment of diabetes mellitus.

Description of the Related Art

Diabetes mellitus is a chronic metabolic disorder causes by insufficient insulin secretion or the ineffective use of glucose in the tissue of an organism, which will leads to excessively high level of blood glucose. It is known that insulin is secreted by pancreatic β cells. Insulin is effective in regulating the blood sugar and may stimulate the glucose transport in adipose cells and muscle cells. Obesity, aging and other reasons may cause insufficient insulin secretion or poor insulin sensitivity, resulting in the increase of blood glucose level and diabetes mellitus. Patients of diabetes mellitus may suffer from symptoms such as, laziness, thirst, excessive urination, blurred vision, and weight loss. Long-term high blood sugar levels may lead to the dysfunction and failure of various organs.

Diabetes mellitus can be primarily classified into Type 1 diabetes and Type 2 diabetes. Type 1 diabetes, also known as insulin dependent diabetes mellitus, is caused by an infection or environmental toxins which trigger the patient's own immune system to attack pancreatic β cells. As a result, pancreatic β cells are damaged, resulting in absolute insulin deficiency and causing blood sugar levels to rise. Type I diabetes accounts for approximately 5% to 10% of all patients with diabetes mellitus. Most patients of Type 1 diabetes are diagnosed before the age of 30, and thus Type 1 diabetes is also known as juvenile diabetes mellitus.

Type II diabetes is also known as non-insulin dependent diabetes mellitus. Most patients of Type II diabetes are diagnosed after the age of 40, and thus, it is also known as adult-onset diabetes mellitus. Type II diabetes accounts for approximately 90% to 95% of all patients with diabetes mellitus. Type II diabetes is caused by the resistance to insulin occurring in cells, which gradually decreases the secretion of insulin from pancreatic β cells and causes a diabetic metabolic disorder. Patients of Type II diabetes often simultaneously suffer from hyperlipidemia, obesity and other symptoms. The risk factors of Type II diabetes includes genetic abnormalities, family history of diabetes, age, obesity (especially abdominal obesity), less physical activity, gestational diabetes, and impaired glucose homeostasis, etc.

The prevalence of diabetes mellitus has increased yearly. According to the World Health Organization in 2008, it is expected that in 2030, there will be over 300 million people with diabetes mellitus globally. Currently, the methods used in the clinical treatments of diabetes mellitus including exercise, diet, and drug treatment. Drug treatment includes insulin injection, oral hypoglycemic drugs, such as sulfonylurea drugs (sufonylureas), biguanide drugs (biguanides), α-glucosidase inhibitor, and insulin sensitizers, etc.

The inventors of the present invention found that a compound of formula (I) has an excellent effect on increasing the expression of SIRT1 (sirtuin 1) mRNA and/or decreasing the expression of SOCS3 (suppressor of cytokine signaling 3) mRNA, and is effective in lowering blood glucose, and thus, can be used for regulating the blood glucose level in a subject in need thereof, especially for treating Type I diabetes and/or Type II diabetes in a subject in need thereof:

(1)

wherein X is H or C1-C3 alkyl; one of Y and Z is and the other one is H, OH or wherein when Y is

Z is and R1 to R13 are independently H or OH, wherein, R1 to R3 are not simultaneously H, and R8 and R9 are not simultaneously H. Preferably, the compound of formula (I) is at least one of compound (1) and compound (2) as follows and can be obtained from a plant extract, such as a *Cistanche tubulosa* extract, (1)

Glu: Glucose
Rha: Rhamnose (2)

Rha: Rhamnose

*Cistanche tubulosa* extract belongs to genus *Cistanche*. The active components of *Cistanche tubulosa* primarily are phenylethanoid glycosides, including echinacoside, acteoside, and isoacteoside. A research team of Shanghai University of Traditional Chinese Medicine (China) conducted in vitro glucose consumption assay with the use of liver cells and conducted in vivo drug-induced hypoglycemic efficacy trials with the use of mice having type I diabetes or type II diabetes induced by different medicaments. The results showed that acteoside obtained from plantago is effective in promoting the consumption of glucose and can decrease the fasting blood glucose level by enhancing the serum insulin level (see Chinese patent publication no. CN 102283854 A, which is entirely incorporated herein by reference). Therefore, in the present invention, the active ingredients of *Cistanche tubulosa* extract were determined by using an animal model of diabetes mellitus and a hepatic glucose consumption test.

SUMMARY OF THE INVENTION

An objective of the present invention is to provide the use of an active component in the manufacture of a medicament, wherein the medicament is for increasing the expression of SIRT1 mRNA and/or decreasing the expression of SOCS3 mRNA, and can be used for regulating the blood glucose level in a subject in need thereof. The active component is selected from the group consisting of a compound of formula (I), a pharmaceutically acceptable salt of the compound of formula (I), and combinations thereof, (1)

wherein X is H or C1-C3 alkyl; one of Y and Z is and the other one is H, OH or wherein when Y is

Z is and R1 to R13 are independently H or OH, wherein, R1 to R3 are not simultaneously H, and R8 and R9 are not simultaneously H.

Another objective of the present invention is to provide a method for increasing the expression of SIRT1 mRNA and/or decreasing the expression of SOCS3 mRNA, or regulating the blood glucose level in a subject in need thereof, comprising administering to the subject an effective amount of an active component selected from the group consisting of a compound of formula (I), a pharmaceutically acceptable salt of the compound of formula (I), and combinations thereof.

The detailed technology and preferred embodiments implemented for the present invention are described in the following paragraphs accompanying the appended drawings for people skilled in this field to well appreciate the features of the claimed invention.

DETAILED DESCRIPTION OF THE INVENTION

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the" or the like recited in the specification of the present invention (especially in the claims) should include both the singular and plural forms. Furthermore, the term "an effective amount" used in this specification refers to the amount of the compound that can at least partially alleviate the condition that is being treated in a suspected subject when administered to the subject. The term "subject" used in this specification refers to a mammalian, including human and non-human animals. The term "treat" or "treating" includes the prevention of particular diseases and/or disorders, the amelioration of particular diseases and/or disorders, and/or the prevention or elimination of the diseases and/or disorder. The term "regulating the blood glucose level in a subject" refers to changing the concentration of blood glucose in a subject towards a normal value. The unit "mg/kg-body weight" used in this specification means the dosage required per kg-body weight.

The present invention provides the use of an active component in the manufacture of a medicament, wherein the medicament is for increasing the expression of SIRT1 mRNA and/or decreasing the expression of SOCS3 mRNA, or regulating the blood glucose level in a subject in need thereof, and the active component is selected from the group consisting of a compound of formula (I), a pharmaceutically acceptable salt of the compound of formula (I), and combinations thereof, (1)

wherein X is H or C1-C3 alkyl; one of Y and Z is and the other one is H, OH or wherein when Y is

Z is and R1 to R13 are independently H or OH, wherein, R1 to R3 are not simultaneously H, and R8 and R9 are not simultaneously H. In formula (I), preferably, X is C1-C3 alkyl, such as methyl, ethyl, linear propyl or branched propyl; both Y and Z are not H; and/or two of R1 to R3 are OH. X is more preferred to be methyl.

In one preferred embodiment of the present invention, the compound of formula (I) is of structure formula (A) as follows:

(A)

wherein Xa is H or C1-C3 alkyl; and R1a to R13a are independently H or OH, wherein R1a to R3a are not simultaneously H, and R8a and R9a are not simultaneously H.

In formula (A), preferably, Xa is C1-C3 alkyl such as methyl, ethyl, linear propyl or branched propyl; and two of R1a to R3a are OH. More preferably, Xa is methyl. Even more preferably, Xa is methyl, two of R1a to R3a are OH, and both R8a and R9a are OH. An embodiment of the compound of formula (A) is compound (1) (i.e., echinacoside):

(1)

Glu: Glucose
Rha: Rhamnose

In another preferred embodiment of the present invention, the compound of formula (I) is of structure formula (C):

(C)

wherein Xc is H or C1-C3 alkyl; Yc is H, OH or and R1c to R13c are independently H or OH, wherein, R1c to R3c are not simultaneously H, and R8c and R9c are not simultaneously H.

In formula (C), preferably, Xc is C1-C3 alkyl such as methyl, ethyl, linear propyl or branched propyl; and two of R1c to R3c are OH. More preferably, Xc is methyl. Even more preferably, Xc is methyl, two of R1c to R3c are OH, and both R8c and R9c are OH. An embodiment of the compound of formula (C) is compound (2) (i.e., isoacteoside):

(2)

Rha: Rhamnose

Therefore, in some embodiments of the present invention, an active component is used in the manufacture of a medicament for increasing the expression of SIRT1 mRNA and/or decreasing the expression of SOCS3 mRNA, or regulating the blood glucose level in a subject in need thereof, wherein the active component is selected from the group consisting of compound (1), a pharmaceutically acceptable salt of compound (1), compound (2), a pharmaceutically acceptable salt of compound (2), and combinations thereof, (1)

Glu: Glucose
Rha: Rhamnose (2)

Rha: Rhamnose

Examples of a pharmaceutically acceptable salt of the above motioned active components include, but are not limited to, alkali metal salts, such as sodium salt, potassium salt.

According to the present invention, the medicament for increasing the expression of SIRT1 mRNA and/or decreasing the expression of SOCS3 mRNA, or regulating the blood glucose level in a subject in need thereof can be manufactured with the use of an active component selected from the group consisting of compound (1), compound (2), and combinations thereof. In these embodiments, the active component can be provided by extracting a plant such as *Cistanche tubulosa* and thus, the active component can be used as an extract.

A *Cistanche tubulosa* extract comprising compound (1) and/or compound (2) can be prepared by a method comprising the following steps: (a) extracting *Cistanche tubulosa* with a polar solvent to provide an extract solution; and (b) optionally drying the extract solution. The polar solvent is water and/or a C1-C4 alcohol, such as methanol, ethanol, ethylene glycol, propanol, isopropanol, propylene glycol, n-butanol, isobutanol, t-butanol, butylene glycol or a combination thereof.

The polar solvent is preferred to be selected from the group consisting of water, methanol, ethanol, and combinations thereof. The polar solvent is more preferred to be water, ethanol, or a combination thereof. The amount of the polar solvent and *Cistanche tubulosa* may be optionally adjusted. In general, the volume ratio between the polar solvent and *Cistanche tubulosa* may range from about 1:1 to about 50:1, and preferably about 20:1.

There is no limitation on the parts of *Cistanche tubulosa* for used in providing the *Cistanche tubulosa* extract. For example, the *Cistanche tubulosa* extract can be provided from extracting the stem, flower, or the whole plant of *Cistanche tubulosa*. According to one embodiment of the present invention, the succulent stem of *Cistanche tubulosa* was used to provide the extract.

In step (a), the extraction is carried out for a period of time to achieve the desired extraction efficiency. For example, when water is used as the polar solvent, the extraction time is usually at least 15 minutes, preferably at least 30 minutes, and more preferably at least 60 minutes. Optionally, the extraction may be accompanied with other appropriate extracting approaches (e.g., stewing, cooling, filtration, concentrated under reduced pressure, and resin column chromatography, etc.) to enhance the efficiency of extraction. Optionally, one may repeat the extraction step (a) one or more times with the same or different solvent(s), and combine all the liquid phase thus obtained to provide the extract solution for step (b) to extract as much active components contained in the plant as possible. Furthermore, one may repeat the cycle of step (a) and step (b) for one or more times to remove as much inactive components as possible.

In one embodiment in accordance with the present invention, a *Cistanche tubulosa* extract was prepared by a method as follows. *Cistanche tubulosa* was soaked in water, stewed, and filtered, and the cycle was repeated three times. The filtrates from different cycles were combined and concentrated under vacuum to provide a concentrate with a specific gravity of 1.10. Thereafter, ethanol was added into the concentrate to a concentration of 60%, and then refrigerated for 12 hours. The supernatant was collected and concentrated under vacuum to provide a crude extract with a specific gravity of 1.10 and the ethanol was recovered. Then, the crude extract was dissolved in hot water with the same volume as the crude extract to provide a mixture. The mixture was injected into a macro-pore absorption resin column for purification. The column was sequentially eluted with water and ethanol. The ethanol eluent was collected and dried by concentration to provide a *Cistanche tubulosa* extract. The *Cistanche tubulosa* extract thus provided comprises a relatively large amount of compound (1) and a relatively small amount of compound (2).

According to the present invention, the medicament manufactured with the use of a compound of formula (I), a pharmaceutically acceptable salt of the compound of formula (I), or a combination thereof, can be used for increasing the expression of SIRT1 mRNA and/or decreasing the expression of SOCS3 mRNA, and especially can be used for regulating the blood glucose level in a subject in need thereof, such as Type I diabetes mellitus and/or Type II diabetes mellitus. It has been known that SIRT1 can promote pancreatic β cells to secrete insulin and can regulate the related factors that cause insulin resistance, such as free radicals and inflammatory factors, and thereby, improve the conditions caused by insulin resistance. In addition, it has been known that the expression level of SOCS-3 can be used as an indicator of leptin resistance. Therefore, without being limited by the theory, it is believed that the medicament provided by the present invention can be used for regulating the blood glucose level in a subject in need thereof by increasing the expression of SIRT1 mRNA and/or decreasing the expression of SOCS3 mRNA in the subject, and can be used for treating the diseases related to the expression levels of SIRT1, such as neuropathy (e.g., Alzheimer's disease (AD), Parkinson's disease (PD), Huntington's disease (HD), amyotrophic lateral sclerosis (ALS), etc.), cardiovascular diseases (e.g., heart disease, hypotension, hypertension, hyperglycemia, stroke, myocardial infarction, thrombosis, arteriosclerosis, etc.), and obesity.

Depending on the requirements of the subject, the medicament according to the present invention can be administered at any suitable dosage. For example, when being administered by a human for regulating the blood glucose level, the medicament is administered at an amount ranging from about 0.5 mg to about 100 mg (as the compound of formula (I))/kg-body weight per day, and preferably about 1 mg to about 55 mg (as the compound of formula (I))/kg-body weight per day. However, for patients with acute conditions, the dosage can be increased to several times or several tens of times, depending on the practical requirements.

According to the present invention, the medicament can be in any suitable form for administration, and be applied in any suitable way. For example, the medicament can be manufactured into a form that is suitable for oral administration, nasal administration, intravenous injection, subcutaneous injection and/or other methods. Because a medicament in an oral administration form is convenient for self-administration, in one preferred embodiment of the present invention, the medicament is provided in an oral administration form such as a tablet, a capsule, a granule, powder, a fluid extract, a solution, syrup, a suspension, an emulsion, a tincture, etc. Depending on the form and purpose, the medicament can further comprise a pharmaceutically acceptable carrier.

Using the manufacturing of a medicament suitable for oral administration as an example, the medicament may comprise a pharmaceutically acceptable carrier which has no adverse effect on the desired activity of the active component (i.e., the compound of formula (I) and/or a pharmaceutically acceptable salt of the compound of formula (I)), such as a solvent, oily solvent, diluent, stabilizer, absorption delaying agent, disintegrant, emulsifier, antioxidant, binder, lubricants, and moisture absorbent. The medicament can be prepared into an oral administration form by any suitable methods.

As for a medicament suitable for subcutaneous injection or intravenous injection, the medicament may comprise one or more components such as an isotonic solution, a saline buffer solution (e.g., a phosphate buffer or a citric acid salt buffer), a solubilizer, an emulsifier, and other carriers to manufacture the composition as an intravenous injection, an emulsion intravenous injection, a powder injection, a suspension injection, or a powder-suspension injection.

In addition to the above adjuvants, the medicament may optionally comprise other additives, such as a flavoring agent, a toner, a coloring agent, etc. to enhance the taste and visual appeal of the resultant medicament. To improve the storability of the resultant formulation, the medicament may also comprise a suitable amount of a preservative, a conservative, an antiseptic, an anti-fungus reagent, etc. Furthermore, the medicament of the present invention may comprise one or more other active components, such as an antioxidant (e.g., vitamin E), insulin sensitizers, etc., to further enhance the efficacy of the medicament or to increase the application flexibility and adaptability of the medicament, as long as the other active components have no adverse effect on the compound of formula (I) and/or a pharmaceutically acceptable salt of the compound of formula (I).

Depending on the requirements of the subject, the medicament according to the present invention can be applied with various administration frequencies, such as once a day, several times a day, or once for days, etc.

The present invention also provide a method for regulating the blood glucose level in a subject in need thereof, comprising administering to the subject an effective amount of an active component selected from the group consisting of a compound of formula (I), a pharmaceutically acceptable salt of the compound of formula (I), and combinations thereof. The choice of the active component and its properties, and the formulations and dosages of the active component are all in line with the above descriptions.

The present invention will be further illustrated in details with specific examples as follows. However, the following examples are provided only for illustrating the present invention, and the scope of the present invention is not limited thereby.

Example 1: Preparation of *Cistanche Tubulosa* Extract 10 kg succulent stem of *Cistanche tubulosa* were sliced and soaked in eight times the volume of water for 1 hour, stewed for 2 hours, and then filtered. The filtrate was collected. The dregs were mixed with six times the volume of water and stewed twice at 1 hour each time, and then filtered. Three obtained filtrates were added together, and then concentrated under vacuum at 50° C. to a specific gravity of 1.10. Thereafter, ethanol was added into the concentrate to a concentration of 60%, and refrigerated for 12 hours. The clear supernatant liquid was collected and concentrated under vacuum at 50° C. to provide a crude extract with a specific gravity of 1.10 and the ethanol was recovered. 6 kg of a crude extract were obtained. Then, the crude extract was dissolved in hot water with the same volume as the crude extract to provide a mixture. The mixture was injected into a macro-pore absorption resin column. The column was sequentially eluted with four times the volume of water and five times the volume of a 40% ethanol. The water eluent was injected in the macro-pore absorption resin column, and then eluted with three times the volume of water. The obtained water eluent was discarded. The column was then eluted with four times the volume of a 40% ethanol. The two obtained 40% ethanol eluent were collected and dried by concentration to provide 1107 g of a *Cistanche tubulosa* extract.

Figure 1:
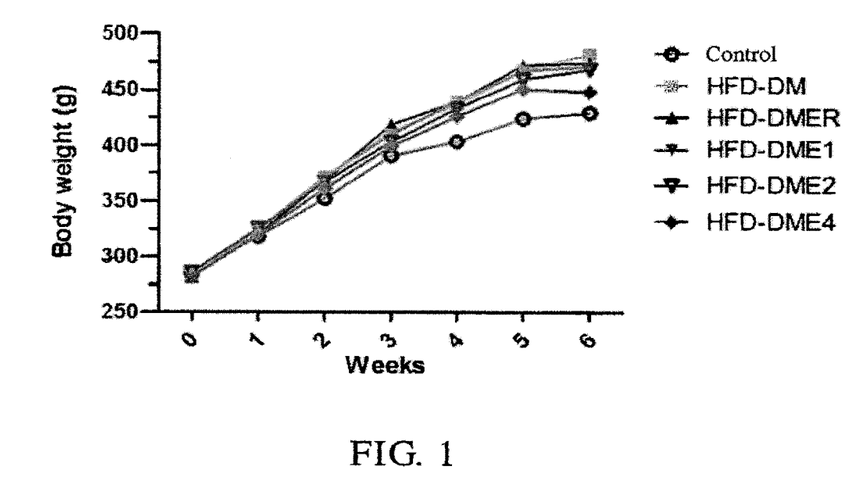
FIG. 1 is a curve diagram showing the body weight of Sprague-Dawley (SD) rats treated with different conditions.
Figure 2:
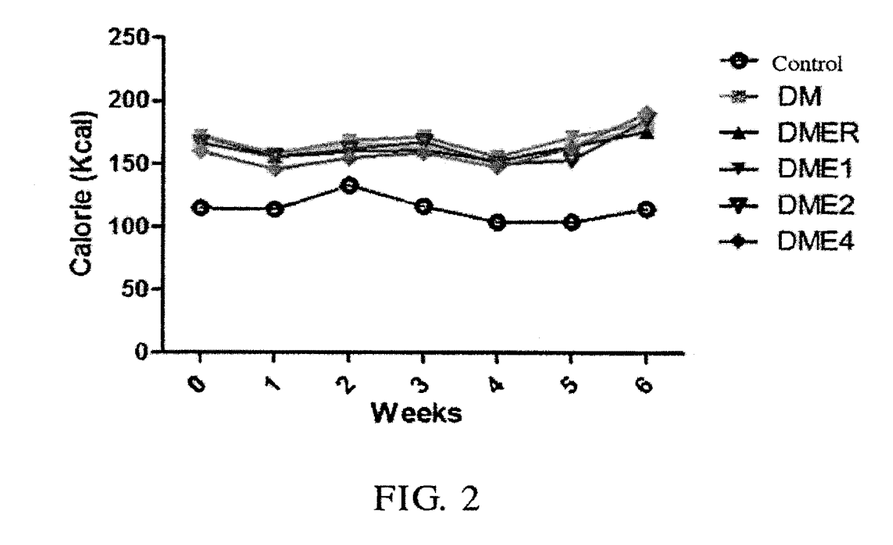
FIG. 2 is a curve diagram showing the caloric intake of SD rats treated with different conditions.

Example 2: Activity Analysis of *Cistanche Tubulosa* Extract (1) Feeding of the Experimental Animals 4-week-old male SD (Sprague-Dawley) rats were fed for one week, and then randomly divided into six groups (10 rats in each group), including five experimental groups and a control group. The rats in the experimental groups were intraperitoneally injected with 230 mg/kg body weight of nicotinamide, and then intraperitoneally injected with 65 mg/kg body weight of streptozocin to induced diabetes mellitus (the DM group). The control group was intraperitoneally injected with the same volume of a citrate buffer (pH 4.5). After a week, the fasting blood glucose of the induced diabetic rats in the experimental groups were measured, to confirmed the fasting blood glucose >126 mg/L. The rats were then fed with a 45% high fat diet (HFD) for 6 weeks. Then, using the dosage shown in Table 1, the rats were orally administered with 0.571 mg/kg body weight of rosiglitazone (a medicine for regulating blood glucose levels, which is an insulin sensitizer) (DMR group) or 80 mg/kg body weight of *Cistanche tubulosa* extract (CTE) (DME1 group), 160 mg/kg body weight of CTE (DME2 group), or 320 mg/kg body weight of CTE (DME4 group), once daily for 6 weeks. The rats in the control group and the DM group were administered with double distilled water once daily for 6 weeks. The body weight of the rats was measured weekly and the caloric intake was calculated. The results are shown in FIG. 1 (body weight) and FIG. 2 (caloric intake). The results show that there is no significant difference between the body weight and caloric intake of the rats in each group.

TABLE 1

| Group | Experimental conditions and administered compound |
| --- | --- |
| Control group | 45% HFD |
| DM | DM + 45% HFD |
| DMR | DM + 0.571 mg/kg body weight rosiglitazone + 45% HFD |
| DME1 | DM + 80 mg/kg body weight CTE + 45% HFD |
| DME2 | DM + 160 mg/kg body weight CTE + 45% HFD |
| DME4 | DM + 320 mg/kg body weight CTE + 45% HFD |

(2) Glucose Tolerance Test

Figure 3:
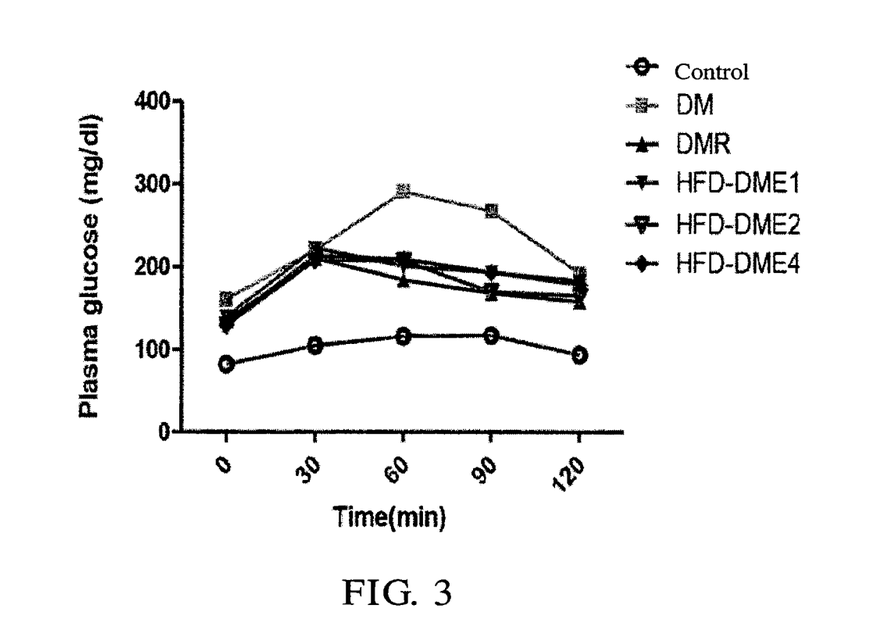
FIG. 3 is a curve diagram showing the plasma glucose concentration of SD rats treated with different conditions.

After the rats were treated for 6 weeks as described above, an oral glucose tolerance test (OGTT) was carried out. The rats were administered with 2 g/kg body weight of glucose, and then the plasma glucose concentration was measured after 0, 30, 90, and 120 minutes to analyze the effect of CTE on the glucose tolerance of the rats after uptake of glucose. The results are shown in FIG. 3. The Area Under Curve (AUC) of FIG. 3 was calculated and shown in FIG. 4.

Figure 4:
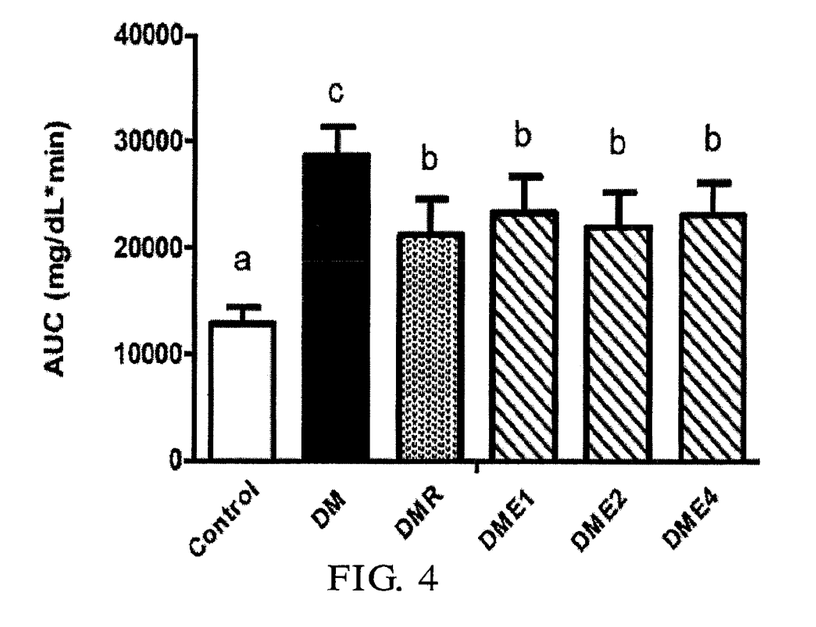
FIG. 4 is a bar diagram showing the area under the curve of plasma glucose concentration of SD rats treated with different conditions.

As shown in FIGS. 3 and 4, as compared to the DM group, the plasma glucose concentration in the rats fed with CTE for 6 weeks (the DME1, DME2, and DME4 group) and the rats in the DMR group were decreased at 0, 30, 90, and 120 minutes. These results show that CTE can effectively increase the glucose uptake rate of the rats, and thus, can lower blood sugar levels.

(3) Analysis of Plasma Samples

After the above glucose tolerance test, the rats were sacrificed, and the blood samples were taken from the celiac artery. The blood samples were centrifuged at 3000 rpm, 4° C. for 15 minutes. The supernatant was collected, which is the plasma. Other tissue of the rats was also taken out and weighed, and then stored at −80° C. for the following biochemical data analysis.

TABLE 2

| | mg/dl(mean ± standard deviation) | | | | | |
|---|---|---|---|---|---|---|
| | Group (n = 10 rats/group) | | | | | |
| | Control group | DM | DMR | DME1 | DME2 | DME4 |
| Fasting blood glucose | 82.2 ± 13.68$^a$ | 160.82 ± 19.71$^c$ | 134.37 ± 17.49$^b$ | 141.68 ± 16.41$^b$ | 129.23 ± 18.74$^b$ | 131.04 ± 15.68$^b$ |
| Total cholesterol | 101.30 ± 27.92 | 104.26 ± 20.92$^b$ | 106.90 ± 19.26$^b$ | 101.85 ± 19.64$^b$ | 104.51 ± 19.78$^b$ | 81.08 ± 11.58$^a$ |
| The total triglyceride | 60.82 ± 15.88$^a$ | 87.07 ± 22.42$^b$ | 62.77 ± 16.05$^a$ | 78.46 ± 29.85$^{ab}$ | 73.44 ± 17.88$^{ab}$ | 56.29 ± 14.74$^a$ |

* One way ANOVA, P < 0.05 as a significance level, post hoc comparisons Dunnett's test after test, wherein "$a$," "$b$," and "$ab$" represent the significant statistical difference between the groups.

(3-1) Determination of Glucose Concentration

20 μl of the plasma was taken and analyzed by a glucose enzymatic kit (FAR EAST GL-V, FAR EAST COMMERCIAL CORP., Japan) to determine the fasting plasma glucose concentration.

The fasting plasma glucose concentration was calculated by the formula as follows:

Fasting plasma glucose concentration (mg/dl)=(Es−blank)/(Estd−blank)×200 wherein Es: absorbance of the blood sample; blank: absorbance of the solvent of the kit (without the blood sample); Estd: absorbance of the standard reagent; 200: concentration of the standard reagent is 200 mg/dl. The results are shown in Table 2.

(3-2) Determination of Total Triglyceride Concentration

10 μl of the plasma was taken and analyzed by a triglyceride enzymatic kit (Audit Diagnostics, Cork, Ireland), to determine the total triglyceride concentration in the plasma. The total triglyceride concentration in the plasma was calculated by the formula as follows:

The total triglyceride concentration in the plasma (mg/dl)=(Es−blank)/(Estd−blank)×200 wherein Es: absorbance of the blood sample; blank: absorbance of the solvent of the kit (without the blood sample); Estd: absorbance of the standard reagent; 200: concentration of the standard reagent is 200 mg/dl. The results are shown in Table 2.

(3-3) Determination of Total Cholesterol Concentration

10 μl of the plasma was taken and analyzed by a cholesterol enzymatic kit (Audit Diagnostics, Cork, Ireland), to determine the total cholesterol concentration in the plasma. The total cholesterol concentration in the plasma was calculated by the formula as follows:

The total cholesterol concentration in the plasma (mg/dl)=(Es−blank)/(Estd−blank)×200 wherein Es: absorbance of the blood sample; blank: absorbance of the solvent of the kit (without the blood sample); Estd: absorbance of the standard reagent; 200: concentration of the standard reagent is 200 mg/dl. The results are shown in Table 2.

As shown in Table 2, as compared to the DM group, the fasting blood glucose in the rats fed with CTE for 6 weeks (the DME1, DME2, and DME4 group) was decreased. The total triglyceride of the DMR group and DME4 group was decreased significantly. It has been known that insufficient insulin concentration or poor insulin sensitivity in patients of diabetes mellitus may cause the abnormal regulation of surrounding adipose tissue, which will result in the decomposition of a large amount of triglycerides in adipose cells. As a result, the concentration of free fatty acids in the blood is increased, resulting in a reduced sensitivity to insulin in peripheral tissues. On the other hand, insulin resistance will lead to the reduction in the use of triglycerides in adipose tissue, resulting in the accumulation of triglycerides in the blood. These results show that CTE is effective in decreasing the concentration of fasting blood glucose and total triglyceride in the diabetic rats, and thus, can lower blood sugar levels.

(3-4) Determination of Insulin Concentration

25 μl of the plasma was taken and analyzed by an insulin ELISA kit (Mercodia AB Inc., Sylveniusgatan 8A, Sweden). The absorbance was measured at 450 nm wavelength by using an ELISA reader, and the concentration was calculated based on the standard curve. The results are shown in Table 3.

(3-5) Determination of Leptin Concentration

Leptin is a protein hormone secreted by adipose cells. It has been known that the imbalance of leptin concentration in the body will cause obesity and the imbalance of insulin. In this experiment, 10 μl of the plasma was taken and analyzed by a leptin enzyme immunoassay kit (Assay Designs, Ins., Ann Arbor, USA). The absorbance was measured at 450 nm wavelength by using an ELISA reader, and the concentration was calculated based on the standard curve. The results are shown in Table 3.

(3-6) Calculation of the Homeostasis Model Assessment Equation of Insulin Resistance The homeostasis model assessment equation of insulin resistance (HOMA-IR) was calculated by the formula as follows:

HOMA-IR=fasting plasma insulin concentration (mU/ml)×fasting plasma glucose concentration (mmole/L)÷22.5

The results are shown in Table 3.

tions shown in DME4 group was closed to that of the control group. These results show that CTE can increase the insulin sensitivity, and decrease leptin resistance and insulin resistance in the rats.

(3-7) Determination of the Concentrations of Urea, Creatinine, Alanine Aminotransferase, and Aspartate Aminotransferase It has been known that diabetes mellitus may cause a lot of complications. In this experiment, the concentrations of the liver and kidney function indicators in the plasma of the rats, including urea, creatinine, alanine aminotransferase (ALT), and aspartate aminotransferase (AST), were analyzed by an UREA detection kit (UR221, Randox, UK), a creatinine detection kit (CR510, Randox, UK), an ALT detection kit (AL 1268, Randox, UK), and an AST detection kit (AS 1267, Randox, UK), respectively. The results are shown in Table 4.

TABLE 3

| | ng/ml (mean ± standard deviation) | | | | | |
| | Group (n = 10 the rats/group) | | | | | |
| | Control group | DM | DMR | DME1 | DME2 | DME4 |
|---|---|---|---|---|---|---|
| Insulin | $3.33 \pm 1.83^a$ | $5.41 \pm 2.28^b$ | $3.57 \pm 2.15^a$ | $3.17 \pm 1.74^a$ | $2.34 \pm 2.03^a$ | $2.28 \pm 1.43^a$ |
| Leptin | $2.97 \pm 1.51^a$ | $7.36 \pm 1.76^b$ | $6.38 \pm 2.05^b$ | $6.26 \pm 2.68^b$ | $3.66 \pm 3.05^a$ | $3.57 \pm 1.71^a$ |
| HOMA-IR | $1.38 \pm 0.70^a$ | $4.43 \pm 1.87^b$ | $2.37 \pm 1.21^a$ | $2.45 \pm 1.79^a$ | $1.62 \pm 1.57^a$ | $1.59 \pm 1.04^a$ |

($\mu g \cdot mmole/L^2$)

*One way ANOVA, P < 0.05 as a significance level, post hoc comparisons Dunnett's test after test, wherein "a" and "b" represent the significant statistical difference between the groups.

As shown in Table 3, as compared to the control group, the plasma insulin concentration, plasma leptin concentration, and HOMA-IR in the rats of the DM group were decreased. As compared to the DM group, the plasma insulin concentration, plasma leptin concentration, and HOMA-IR in the rats fed with CTE for 6 weeks (the DME1, DME2, and DME4 group) was restored (decreased), and the concentra-

TABLE 4

(mean ± standard deviation)
Group (n = 10 the rats/group)

| | Control group | DM | DMR | DME1 | DME2 | DME4 |
|---|---|---|---|---|---|---|
| Urea (mg/dl) | 21.30 ± 4.50$^a$ | 32.90 ± 5.68$^c$ | 19.14 ± 3.92$^a$ | 23.17 ± 6.25$^{ab}$ | 27.14 ± 6.18$^b$ | 20.98 ± 4.21$^a$ |
| Creatinine (mg/dl) | 0.86 ± 0.42$^{ab}$ | 2.13 ± 0.81$^c$ | 1.19 ± 0.32$^b$ | 0.58 ± 0.20$^a$ | 0.72 ± 0.21$^a$ | 0.66 ± 0.26$^a$ |
| AST (U/L) | 32.36 ± 4.65$^a$ | 55.17 ± 23.07$^b$ | 38.24 ± 7.03$^a$ | 30.90 ± 7.90$^a$ | 31.25 ± 4.82$^a$ | 34.98 ± 9.41$^a$ |
| ALT (U/L) | 31.23 ± 5.74$^a$ | 31.54 ± 7.48$^a$ | 29.88 ± 5.77$^a$ | 38.82 ± 7.29$^a$ | 31.84 ± 9.36$^a$ | 30.77 ± 7.68$^a$ |
| AST/ALT | 1.07 ± 0.20$^{ab}$ | 1.76 ± 0.51$^c$ | 1.34 ± 0.38$^b$ | 0.80 ± 0.15$^a$ | 1.06 ± 0.30$^{ab}$ | 1.36 ± 0.43$^b$ |

*One way ANOVA, P < 0.05 as a significance level, post hoc comparisons Dunnett's test after test, wherein "$a$," "$b$," "$ab$," "$c$" represent the significant statistical difference between the groups.

As shown in Table 4, as compared to the control group, the concentrations of urea and creatinine, and the ALT/AST ratio in the rats of the DM group were increased. As compared to the DM group, the plasma urea, the concentrations of the plasma urea, creatinine, and ALT/AST ratio in the rats fed with CTE for 6 weeks (the DME1, DME2, and DME4 group) was significantly restored (decreased).

(3-8) Determination of the Concentration of Plasma Antioxidant Enzymes

It has been known that both Type I diabetes mellitus and Type II diabetes mellitus may cause the decreased expression of antioxidant enzymes in the body, and thus, increases oxidative stress. In this experiment, the concentrations of superoxide dismutase (SOD), catalase, and glutathione peroxidase (GPx) in the plasma of the rats were analyzed by an SOD detection kit, a catalase detection kit, and a GPx detection kit (Eugene-Chen CO., LTD, TW), respectively, to analyze the effect of CTE on the expression levels of antioxidant enzymes. The results are shown in Table 5.

As shown in Table 5, as compared to the control group, the activities of superoxide dismutase, catalase, and gluta- thione peroxidase in the rats of the DM group were decreased. As compared to the DM group, the activities of superoxide dismutase, catalase, and glutathione peroxidase in the rats fed with CTE for 6 weeks (the DME1, DME2, and DME4 group) and the rats in the DMR group were significantly increased. These results show that CTE can increase the expression levels of antioxidant enzymes, and thus, can improve the oxidative stress caused by diabetes mellitus.

(3-9) Determination of Over-Oxidation of Plasma Lipid

It has been known that diabetes mellitus may cause the increased over-oxidation of plasma lipid. Malondialdehyde (MDA) can be used as an indicator of lipid over-oxidation. In this experiment, the concentration of plasma malondialdehyde was determined to analyze the effect of CTE on lipid over-oxidation. 0.5 ml of the plasma was taken and evenly mixed with 1 ml of a reaction reagent (15% w/v % trichloroacetic acid, dissolved in 0.25 N HCl; and 0.375% w/v % thiobarbituric acid, dissolved in 0.25 N HCl). Then, the mixture was placed in a water bath at 100° C. for 15 minutes,

TABLE 5

U/mg protein (mean ± standard deviation)
Group (n = 10 the rats/group)

| | Control group | DM | DMR | DME1 | DME2 | DME4 |
|---|---|---|---|---|---|---|
| Superoxide dismutase | 0.60 ± 0.13$^b$ | 0.40 ± 0.05$^a$ | 0.65 ± 0.15$^b$ | 0.64 ± 0.24$^b$ | 0.63 ± 0.25$^b$ | 0.55 ± 0.03$^{ab}$ |
| Catalase | 81.58 ± 32.37$^b$ | 44.07 ± 6.79$^a$ | 60.05 ± 9.92$^{ab}$ | 68.24 ± 27.80$^b$ | 70.53 ± 33.79$^b$ | 58.29 ± 8.50$^{ab}$ |
| Glutathione peroxidase | 1974.36 ± 609.87$^c$ | 606.41 ± 498.49$^a$ | 811.08 ± 359.72$^{ab}$ | 918.66 ± 228.38$^{ab}$ | 948.06 ± 501.99$^{ab}$ | 1065.95 ± 168.89$^b$ |

*One way ANOVA, P < 0.05 as a significance level, post hoc comparisons Dunnett's test after test, wherein "$a$," "$b$," "$ab$," and "$c$" represent the significant statistical difference between the groups.

and cooled. 1 ml of n-butanol was added thereinto, vigorously shocked mixed and centrifuged (1500×g, 10 minutes).

The supernatant was collected, and its absorbance at 532 nm was measured by using a spectrophotometer, wherein a PBS buffer was used as a blank and 5 nM of 1,1,3,3-tetramethoxypropane was used as a standard. The concentration of plasma malondialdehyde was calculated by the formula as follows:

The concentration of plasma malondialdehyde (nM/ml)=[(absorbance of the sample−blank)/(absorbance of the standard−blank)]×5

Figure 5:
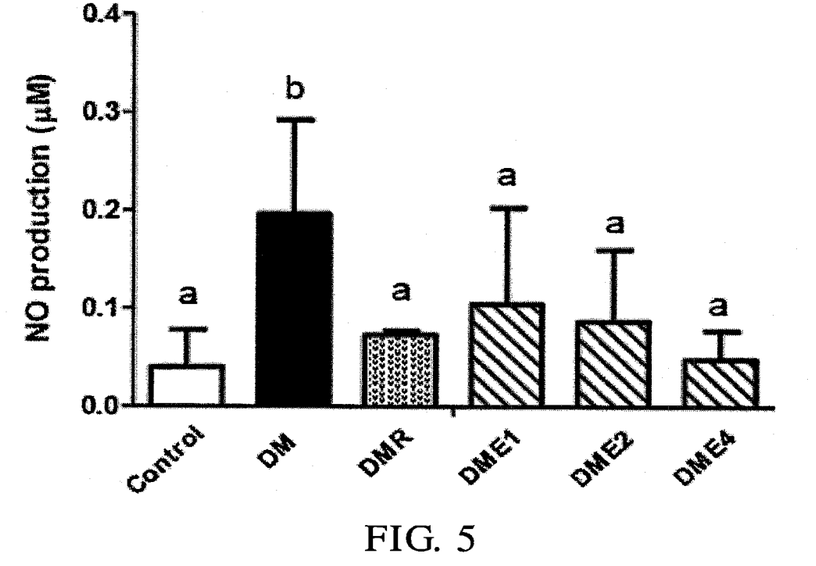
FIG. 5 is a curve diagram showing the plasma nitric oxide (NO) concentration of SD rats treated with different conditions.
Figure 6:
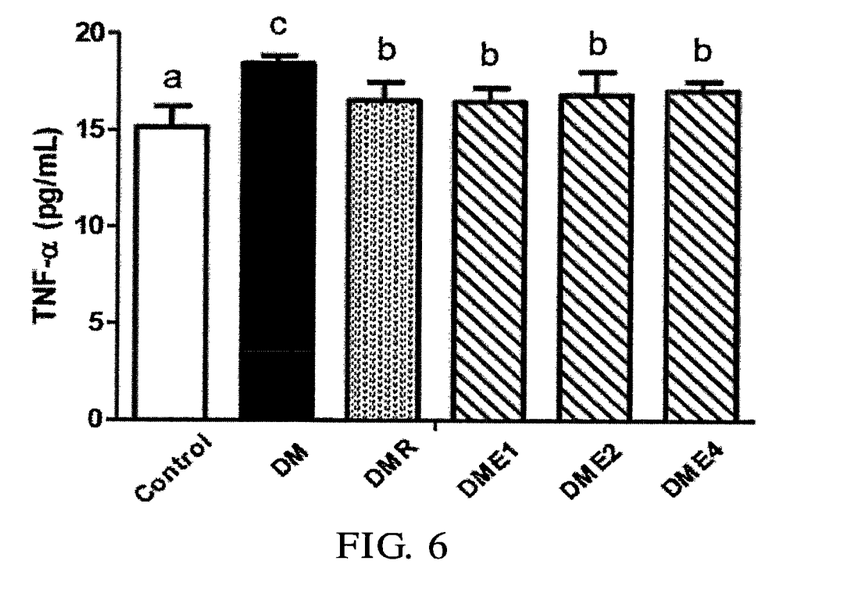
FIG. 6 is a curve diagram showing the plasma TNF-α concentration of SD rats treated with different conditions.
Figure 7:
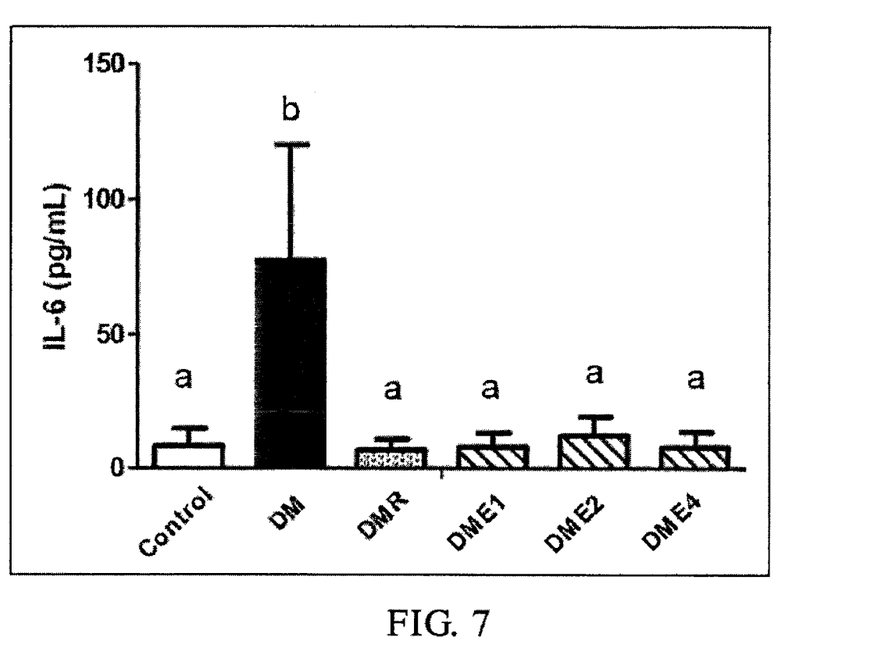
FIG. 7 is a curve diagram showing the plasma IL-6 concentration of SD rats treated with different conditions.

The results are shown in Table 6.

added into each well of the microplate and incubated at room temperature for 30 minutes. Then, the supernatant was discarded, and the microplate was washed with the washing buffer 5 times. 100 µl of a substrate solution was added into each well of the microplate and incubated at room temperature for 15 minutes. 50 µl of a stop solution was added into each well of the microplate, and the absorbance was measured at 450 nm wavelength by using a microplate reader to calculate the concentrations. The results are shown in FIGS. 5 to 7. In FIGS. 5 to 7, post hoc comparisons was used,

TABLE 6

| | nM/ml (mean ± standard deviation) Group (n = 10 the rats/group) | | | | | |
|---|---|---|---|---|---|---|
| | Control group | DM | DMR | DME1 | DME2 | DME4 |
| Malondialdehyde | 10.15 ± 1.20$^a$ | 16.87 ± 2.42$^c$ | 13.38 ± 2.12$^b$ | 9.90 ± 2.09$^a$ | 10.66 ± 1.94$^a$ | 9.95 ± 1.55$^a$ |

*One way ANOVA, $P < 0.05$ as a significance level, post hoc comparisons Dunnett's test after test, wherein "$a$," "$b$," and "$c$" represent the significant statistical difference between the groups.

As shown in Table 6, as compared to the control group, the concentration of plasma malondialdehyde in the rats of the DM group was increased. As compared to the DM group, the concentration of plasma malondialdehyde in the rats fed with CTE for 6 weeks (the DME1, DME2, and DME4 group) was decreased. These results show that CTE is effective in decreasing the lipid over-oxidation caused by diabetes mellitus.

(3-10) Determination of Plasma Inflammatory Indicators

It has been known that the concentration of Advanced Glycation End-products (AGE) in diabetic patients will increase. When free AGEs combine with receptor for advanced glycation end products (RAGE), superoxide radicals will be generated, which will activate downstream NF-κB transcription factors, and thus, result in a series of inflammatory reactions. In this experiment, the concentrations of inflammatory indicators in the plasma, including nitric oxide (NO), TNF-α, and IL-6, were determined to analyze the effect of CTE on inflammation caused by wherein "a," "b," and "c" represent the significant statistical difference between the groups.

As shown in FIGS. 5 to 7, as compared to the control group, the plasma concentrations of NO (FIG. 5), TNF-α (FIG. 6), and IL-6 (FIG. 7) in the rats of the DM group was increased, indicating a serious inflammation. As compared to the DM group, the concentrations of NO, TNF-α, and IL-6 in the rats fed with CTE for 6 weeks (the DME1, DME2, and DME4 group) were decreased. These results show that CTE is effective in decreasing the inflammation caused by diabetes mellitus.

(4) Determination of the Weights of the Liver, Kidney, Heart, and Abdominal Fat of the Rats In this experiment, the weights of the liver, kidney, heart, and abdominal fat of the rats treated with different conditions for 6 weeks were determined. As shown in Table 7, there are no significant differences between the weights of the liver, kidney, heart, and abdominal fat of the rats in different groups.

TABLE 7

| | Percentage (%) compared to body weight (mean ± standard deviation) Group (n = 10 the rats/group) | | | | | |
|---|---|---|---|---|---|---|
| | Control group | DM | DMR | DME1 | DME2 | DME4 |
| Liver | 3.27 ± 0.29$^a$ | 3.51 ± 0.42$^a$ | 3.21 ± 0.31$^a$ | 3.38 ± 0.41$^a$ | 3.22 ± 0.40$^a$ | 3.15 ± 0.23$^a$ |
| Kidney | 0.38 ± 0.03$^a$ | 0.34 ± 0.04$^a$ | 0.34 ± 0.04$^a$ | 0.36 ± 0.07$^a$ | 0.34 ± 0.04$^a$ | 0.36 ± 0.02$^a$ |
| Heart | 0.33 ± 0.03$^a$ | 0.31 ± 0.02$^a$ | 0.34 ± 0.03$^a$ | 0.33 ± 0.04$^a$ | 0.34 ± 0.04$^a$ | 0.33 ± 0.02$^a$ |
| Abdominal fat | 1.45 ± 0.33$^a$ | 2.55 ± 0.75$^b$ | 2.49 ± 0.65$^b$ | 2.30 ± 0.57$^b$ | 2.59 ± 0.72$^b$ | 1.98 ± 0.50$^{ab}$ |

*One way ANOVA, $P < 0.05$ as a significance level, post hoc comparisons Dunnett's test after test, wherein "$a$," "$b$," and "$ab$" represent the significant statistical difference between the groups.

diabetes mellitus. 100 ml of standard solutions of different concentrations or the plasma were added into different wells of a microplate coated with a capture antibody. The microplate was incubated at room temperature for 2 hours, the sample was removed, and then the microplate was washed five times with a 400 µl of a washing buffer (1×PBS, 0.05% Tween 20). 100 µl of the detecting antibodies of NO, TNF-α, and IL-6 were added into the microplate and incubated at room temperature for 1 hour. Then, the supernatant was discarded, and the microplate was washed with the washing buffer 5 times. 480 µl of enzyme avidan-HRP was (5) Determination of the Expression of SIRT1 and SOCS-3

It has been known that the sirtuin 1 (SIRT1) can promote pancreatic β cells to secrete insulin and regulate the related factors that cause insulin resistance, such as free radicals and inflammatory factors, and thereby, improving the insulin resistance. In addition, the expression level of SOCS-3 (suppressor of cytokine signaling 3) can be used as an indicator of leptin resistance. In this experiment, the effect of CTE on the expression levels of SIRT1 mRNA and SOCS-3 mRNA of the rats were discussed. The total RNA of the hypothalamic brain tissue of the rats was extracted by using an RNeasy Lipid Tissue Mini (QIAGEN). 1 μg of the total RNA, 1 μl of 0.5 μg/μl oligo(dT), and DEPC-H$_2$O (to a final volume of 12 μl) were mixed. Then, the mixture were reacted at 65° C. for 5 minutes, and placed on ice for 5 minutes. 4 μl of a 5× first-strand buffer, 1 μl of 10 mM dNTP, and 1 μl HiScript I reverse transcriptase were added thereinto, and then the mixture were reacted at 30° C. for 10 minutes, at 48° C. for 60 minutes, and at 70° C. for 15 minutes. Then, 1 μl of the obtained DNA, 0.5 μl 10 mM dNTPs, 2.5 μl 10× PCR buffer, 0.5 μl of each gene specific primer (GSP), 0.25 μl Taq polymerase, and double distilled water (to a final volume of 25 μl) were mixed, and a polymerase chain reaction (PCR) was conducted at the conditions as follows: denaturation at 94° C. for 5 minutes followed by 40 cycles of denaturation at 94° C. for 30 seconds; annealing at 55° C. for 30 seconds; elongation at 72° C. for 30 seconds. The results are shown in FIGS. 8 and 9.

Figure 8:
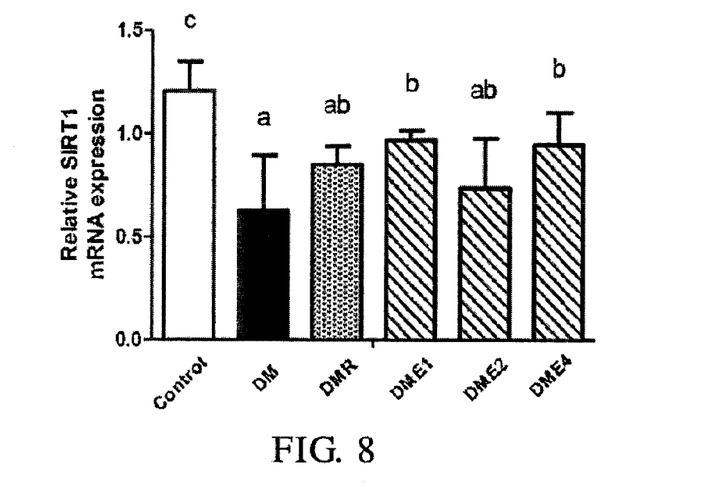
FIG. 8 is a curve diagram showing the SIRT1 mRNA expression level in the hypothalamic brain tissue of SD rats treated with different conditions.
Figure 9:
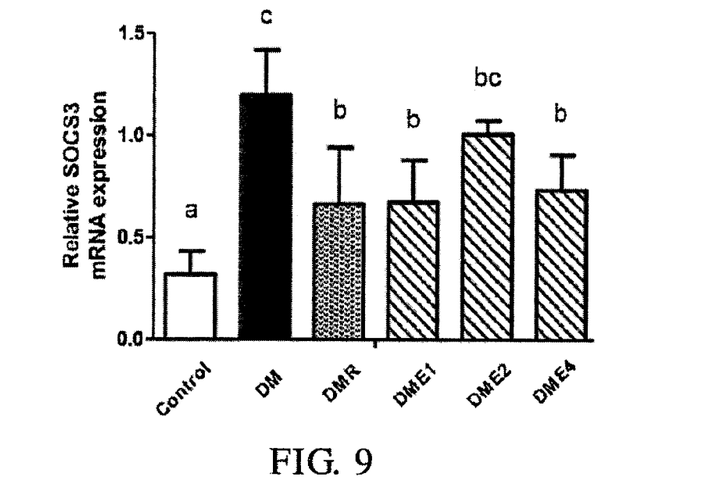
FIG. 9 is a curve diagram showing the SOCS3 mRNA expression level in the hypothalamic brain tissue of SD rats treated with different conditions.

As shown in FIG. 8, as compared to the control group, the SIRT1 mRNA expression level of the diabetic rats (the DM group) is significantly decreased. These results show that CTE can increase the expression level of SIRT1 mRNA of the rats, and thereby, improving insulin resistance. In addition, as shown in FIG. 9, as compared to the control group, the SOCS-3 mRNA expression levels of the rats in the DM group are significantly increased, indicating more severe leptin resistance. As compared to the DM group, the SOCS-3 mRNA expression levels of the rats fed with CTE (DME1, DME2, and DME4 group) were significantly decreased. These results show that CTE can decrease the expression level of SOCS-3 mRNA of the rats, and thereby, improving leptin resistance caused by diabetes mellitus.

Example 3: Analysis of the Components in *Cistanche Tubulosa* Extract

The components in the *Cistanche tubulosa* extract were analyzed by high performance liquid chromatography (HPLC). The experimental conditions were as follows: using an Agilent Zorbax SB-C18 column (2.1×150 mm, 5 μm); the mobile phase was solvent A: acetonitrile (ACN) containing 0.1% formic acid, and solvent B: MQ-H$_2$O containing 0.1% formic acid; a flow rate of 0.3 ml/minutes; detection wavelength was 333 nm. 5 μl of the standards of echinacoside (ChromaDex, US), acteoside (ChromaDex, US), and isoacteoside (ChromaDex, US), and the *Cistanche tubulosa* extract solution (dissolved in 50% methanol) was separately injected into the HPLC system. The peak areas of each sample were determined, and the percentage of echinacoside, acteoside and isoacteoside contained in the *Cistanche tubulosa* extract was calculated based on the peak areas. The results are shown in Table 8.

TABLE 8

| | Component | | |
|---|---|---|---|
| | Echinacoside | Acteoside | Isoacteoside |
| Percentage | 26.2 wt % | 2.6 wt % | 4.4 wt % |

As shown in Table 8, the *Cistanche tubulosa* extract comprises about 26.2 wt % of echinacoside, about 2.6 wt % of acteoside, and about 4.4 wt % of isoacteoside.

Based on the data shown in Table 8, the contents of each active component contained in the CTE administered in the DME1, DME2, DME4 group described in Example 2 are calculated, and the results are shown in Table 9.

TABLE 9

| Dosage (mg/kg) | Echinacoside | Acteoside | Isoacteoside |
|---|---|---|---|
| 80 (DME1 group) | 20.96 | 2.08 | 3.52 |
| 160 (DME2 group) | 41.92 | 4.16 | 7.04 |
| 320 (DME4 group) | 83.84 | 8.32 | 14.08 |

Example 4: Analysis of the Activities of Echinacoside and Isoacteoside

The above experimental data show that the *Cistanche tubulosa* extract comprises echinacoside, acteoside and isoacteoside. In this experiment, the effect of echinacoside, acteoside and isoacteoside on regulating blood glucose levels was further confirmed.

(1) Cell Assay

A carbohydrate consumption assay was conducted by using human hepatocellular liver carcinoma cell line (HepG2, Bioresource Collection and Research Center, BCRC number: 60025). The cells were treated with 1000 μg/ml glucose, and then treated with 100 nM insulin, 50 μg/ml *Cistanche tubulosa* extract (CTE), 12.5 μg/ml of echinacoside, 1.25 μg/ml of acteoside, or 2.25 μg/ml of isoacteoside (i.e., an active component by an amount of what it presents in the extract). After 1 hour, the carbohydrate consumption level was determined. The results are shown in FIG. 10, wherein the data were shown as mean±standard deviation (n=3); ***$P<0.001$ (as compared to the control group).

Figure 10:
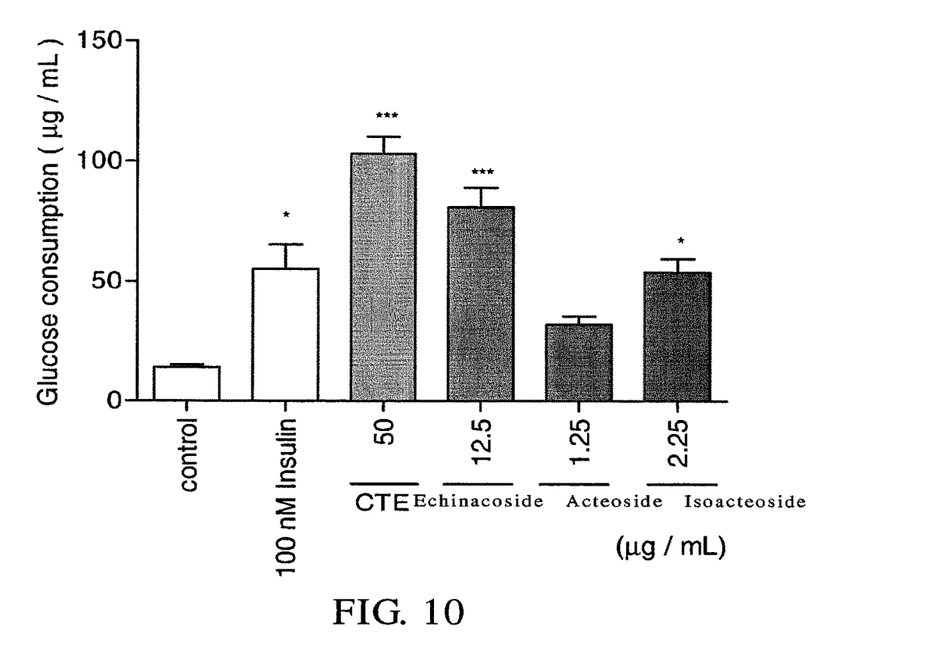
FIG. 10 shows a carbohydrate consumption assay carried out by using liver cells treated with different conditions.

As shown in FIG. 10, as compared to the control group, 50 μg/ml *Cistanche tubulosa* extract and 12.5 μg/ml of echinacoside and 2.25 μg/ml of isoacteoside can effectively increase the carbohydrate consumption level of the liver cells, while the efficacy of 1.25 μg/ml of acteoside was not obvious, which might be due to its low percentage.

(2) Concentration-Dependent Assay

Figure 11:
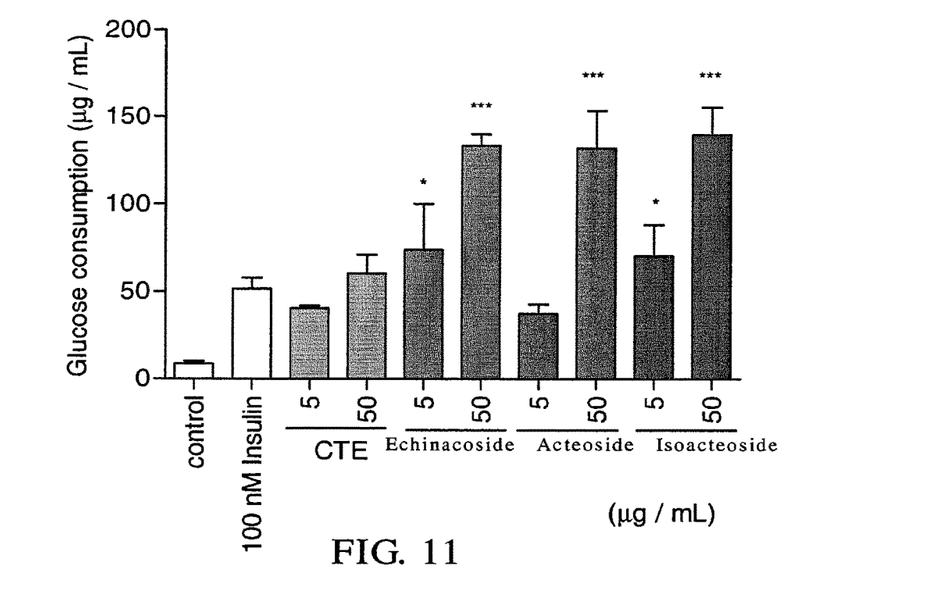
FIG. 11 shows a carbohydrate consumption assay carried out by using liver cells treated with different conditions (showing dose dependence).

To further confirm if the active components that are present in *Cistanche tubulosa* extract have the effect of accelerating liver cells to uptake blood sugar, a carbohydrate consumption assay as described above was conducted by using different concentrations of *Cistanche tubulosa* extract, echinacoside, acteoside and isoacteoside to treated the HepG2 cells. The results are shown in FIG. 11, wherein the data were shown as mean±standard deviation (n=3); $P<0.01$; *$P<0.001$ (as compared to the control group); #$P<0.05$ (as compared to the insulin group).

As shown in FIG. 11, as compared to the control group, 5 μg/ml, and 50 μg/ml of *Cistanche tubulosa* extract (CTE), echinacoside, acteoside and isoacteoside can effectively increase the carbohydrate consumption level of the liver cells, and the results showed a dose dependence, wherein the result of acteoside is similar to previous researches, showing that acteoside can increase the carbohydrate consumption level of liver cells. Furthermore, the results of this experiment show that echinacoside and isoacteoside can increase the carbohydrate consumption level of liver cells at a very low concentration, such as 5 μg/ml. The results of this experiment also show that the effect of *Cistanche tubulosa* extract in increasing the carbohydrate consumption level of liver cells and thus in lowering blood sugar levels is primarily attributable to echinacoside and acteoside contained therein, but not acteoside.

The above results show that *Cistanche tubulosa* extract and the echinacoside and isoacteoside contained therein are effective in lowering blood sugar levels, and thus, can be used for regulating blood glucose levels, especially for treating Type I and Type II diabetes mellitus.

What is claimed is:

1. A method for treating Type 1 diabetes mellitus in a subject in need thereof, comprising administering to the subject an effective amount of an active component selected from the group consisting of a compound (2), a pharmaceutically acceptable salt of compound (2), and combinations thereof:

(2)

Rha: Rhamnose

2. The method as claimed in claim 1, wherein the active component is used as an extract.

3. The method as claimed in claim 2, wherein the extract is a *Cistanche tubulosa* extract.

4. The method as claimed in claim 3, wherein the *Cistanche tubulosa* extract is prepared by a method comprising:

(a) extracting *Cistanche tubulosa* with a polar solvent to provide an extract solution; and (b) optionally drying the extract solution, wherein the polar solvent is selected from the group consisting of water, C1-C4 alcohols, and combinations thereof.

5. The method as claimed in claim 4, wherein the polar solvent is selected from the group consisting of: water, methanol, ethanol, and combinations thereof.

6. The method as claimed in claim 1, wherein the active component is administered at an amount ranging from about 0.5 mg (as the compound (2))/kg-body weight to about 100 mg (as the compound (2))/kg-body weight per day.

7. The method as claimed in claim 1, wherein the active component is administered at an amount ranging from about 1 mg (as the compound (2))/kg-body weight to about 55 mg (as the compound (2))/kg-body weight per day.

8. The method as claimed in claim 1, wherein the active component treats diabetes mellitus by increasing the expression of SIRT1 mRNA, and/or decreasing the expression of SOCS3 mRNA.

* * * * *